United States Patent [19]

Boguth et al.

[11] 4,393,073

[45] Jul. 12, 1983

[54] PHARMACEUTICAL PREPARATIONS

[75] Inventors: Walter Boguth, Riehen; Georges Hirth, Huningue, both of France

[73] Assignee: Hoffmann-La Roche Inc., Nutley, N.J.

[21] Appl. No.: 371,621

[22] Filed: Apr. 26, 1982

Related U.S. Application Data

[62] Division of Ser. No. 228,792, Jan. 27, 1981, Pat. No. 4,339,447.

[30] Foreign Application Priority Data

Feb. 7, 1980 [CH] Switzerland ............................ 983/80

[51] Int. Cl.³ ...................... A61U 31/07; A61U 31/12; A61U 31/33; A61U 31/355
[52] U.S. Cl. ................................... 424/284; 424/229; 424/244; 424/251; 424/331; 424/344
[58] Field of Search ........................ 424/331, 384, 344

[56] References Cited

U.S. PATENT DOCUMENTS 1,752,305  4/1930  Lautenschläger et al. ......... 424/333

FOREIGN PATENT DOCUMENTS 2058826  7/1972  Fed. Rep. of Germany .
2252637  5/1974  Fed. Rep. of Germany .
1752305  9/1978  France .

OTHER PUBLICATIONS

Chem. Abst., 81—63145u (1974).
Chem. Abst., 82—125789p (1975).
Merck Index, 9th Ed. (1976), No. 2961.

*Primary Examiner*—Stanley J. Friedman
*Attorney, Agent, or Firm*—Jon S. Saxe; George M. Gould; Peter R. Shearer

[57] ABSTRACT

Pharmaceutical preparations containing glycerol alkyl ethers as the solvent.

6 Claims, No Drawings

PHARMACEUTICAL PREPARATIONS

This is a division of application Ser. No. 228,792, filed Jan. 27, 1981, now U.S. Pat. No. 4,339,447.

BACKGROUND OF THE INVENTION

The solvents hitherto proposed and used for pharmaceutical preparations are not entirely satisfactory in view of their various properties, for example the dissolving power, the miscibility with other solvents and especially the physiological compatability. The disadvantages of such commercial pharmaceutical solvents are described, for example, in German Auslegeschrift No. 2 708 419. In said Auslegeschrift there are described the advantageous properties of 1,2-butanediol 1-methyl ether as the solvent for pharmaceutical purposes. It has, meanwhile, been established that this compound produces changes in the blood.

SUMMARY OF THE INVENTION

It has now been found in accordance with the present invention that glycerol lower-alkyl ethers are especially suitable solvents for pharmaceutical purposes since they exhibit a very good dissolving power, are miscible with other pharmaceutical solvents and have a better physiological compatability than 1,2-butanediol 1-methyl ether.

DETAILED DESCRIPTION OF THE INVENTION

The present invention is directed to pharmaceutical preparations containing a glycerol lower-alkyl ether as the solvent. The invention is also directed to the use of lower-alkyl ethers as the solvent in pharmaceutical preparations. This invention is especially adapted to preparing injectable solutions containing a pharmaceutically-active ingredient.

The term "lower alkyl" as used in this application designates straight- or branched-chain saturated aliphatic hydrocarbon groups containing from 1 to 7 carbon atoms such as methyl, ethyl, n-propyl, isopropyl, n-butyl, isobutyl, t-butyl, etc.

In accordance with this invention, the pharmaceutical preparations contain a pharmaceutically-active ingredient and a solvent containing a glycerol lower-alkyl ether.

In accordance with this invention, any conventional pharmaceutically-active ingredient which is soluble in a glycerol lower-alkyl solvent can be utilized to prepare the pharmaceutical preparations.

Glycerol mono(lower-alkyl) ethers and glycerol di(-lower-alkyl) ethers are especially suitable for the purpose of the present invention. Examples of such ethers are glycerol 1-methyl ether, glycerol 1-ethyl ether, glycerol 1,2-dimethyl ether and glycerol 1,3-dimethyl ether. Glycerol 1-methyl ether, glycerol 1,3-dimethyl ether and, especially, glycerol 1,2-dimethyl ether are particularly preferred.

Among the pharmaceutically-active ingredients contained in the pharmaceutical preparations of this invention are sulphonamides, for example sulphamethoxazole, sulphadoxine, sulphamoxole or sulphathiazine; conveniently in the form of pharmaceutically-acceptable salts; sulphonamide potentiators, for example trimethoprim or diaveridine; benzodiazepines, for example diazepam, oxazepam or chlordiazepoxide; or vitamins, for example vitamin A acetate, vitamin $K_1$ or vitamin E.

Of particular interest are pharmaceutical preparations which contain sulphamethoxazole, trimethoprim and glycerol 1-methyl ether or diazepam and glycerol 1,1-dimethyl ether.

The solvent can be 100% by volume of the glycerol lower-alkyl ether. Generally, it is preferred that the solvent contain at least 50% by volume of the glycerol lower-alkyl ether. The solvent can contain other compatible ingredients such as water or ethanol. Among the preferred solvents are those which contain from about 50% to 80% by volume of the glycerol lower-alkyl ether and from about 20% to 50% by volume of water. Among the other preferred solvent mixtures are those containing from about 50% to 80% by volume of the glycerol lower-alkyl ether, 20% to 50% by volume of water and 5% to 10% by volume of ethanol. Furthermore, it has been found that in the case of pharmaceutical preparations which have a high water content and which contain an active substance difficultly soluble in water, the stability during storage can be improved when said preparations are heated for a short time (e.g., at 120° C. for 10 minutes).

The pharmaceutical preparations provided by the present invention can be manufactured by dissolving a pharmaceutically-active substance in a glycerol lower-alkyl ether, if desired, with the addition of water or water and ethanol.

The pharmaceutical preparations provided by the present invention are especially suitable for use as injection solutions; for example, for the intravenous or intramuscular administration of pharmaceutically-active substances.

The following examples illustrate the present invention:

EXAMPLE 1

1 g of sulphamethoxide is dissolved in 1 ml of 4 N sodium hydroxide while warming slightly. 0.2 g of trimethoprim in 3.5 ml of glycerol 1-methyl ether is added to this solution while stirring, a clear solution resulting. If desired, this solution is filtered sterile and filled into ampoules.

EXAMPLE 2

10 mg of diazepam are dissolved in 1.2 ml of glycerol 1,2-dimethyl ether. The solution is treated with 0.8 ml of water and, if desired, filtered sterile and filled into ampoules.

EXAMPLE 3

10 mg of diazepam are dissolved in 1.5 ml of glycerol 1-methyl ether. The solution is mixed with 0.5 ml of water and, if desired, filtered sterile and filled into ampoules.

EXAMPLE 4

10 mg of diazepam are dissolved in 1.2 ml of glycerol 1-ethyl ether. The solution is mixed with 0.8 ml of water and, if desired, filtered sterile and filled into ampoules.

EXAMPLE 5

15 mg of vitamin A acetate are dissolved in 1 ml of glycerol 1-methyl ether. If desired, the solution is filtered sterile and filled into ampoules.

EXAMPLE 6

200 mg of vitamin $K_1$ are dissolved in 1 ml of glycerol 1,2-dimethyl ether. If desired, the solution is filtered sterile and filled into ampoules.

EXAMPLE 7

200 mg of vitamin E are dissolved in 1 ml of glycerol 1,2-dimethyl ether. If desired, the solution is filtered sterile and filled into ampoules.

EXAMPLE 8

1 g of sulphamethoxazole is dissolved in 1 ml of 4 N sodium hydroxide while warming slightly. To this solution is added with the good intermixing 0.2 g of trimethoprim in 3.05 ml of glycerol 1-methyl ether and 0.45 ml of rectified alcohol, there being obtained a clear solution.

EXAMPLE 9

1 g of sulphadoxime is dissolved in 1 ml of 3.3 N sodium hydroxide while warming slightly. To this solution is added with good intermixing 0.2 g of trimethoprim in 3.05 ml of glycerol 1-methyl ether and 0.45 ml of rectified alcohol, there being obtained a clear solution.

EXAMPLE 10

10 mg of diazepam are dissolved in 0.9 ml of glycerol 1,2-dimethyl ether and 0.1 ml of rectified alcohol and treated with good intermixing with 1 ml of physiological sodium chloride solution. A clear solution is obtained.

EXAMPLE 11

10 mg of diazepam are dissolved in 0.8 ml of glycerol 1,3-dimethyl ether and 0.1 ml of rectified alcohol and treated with good intermixing with 1.1 ml of physiological sodium chloride solution. A clear solution is obtained.

EXAMPLE 12

10 mg of diazepam are dissolved in 0.9 ml of glycerol 1-ethyl ether and 0.1 ml of rectified alcohol and combined with 1.0 ml of physiological sodium chloride solution to give a clear solution.

EXAMPLE 13

10 mg of diazepam are dissolved in 1.0 ml of glycerol 1-methyl ether and 0.1 ml of rectified alcohol and mixed with 0.9 ml of physiological sodium solution to give a clear solution.

EXAMPLE 14

15 mg of vitamin A acetate are dissolved in 1 ml of glycerol 1-methyl ether at room temperature, there being obtained a clear solution.

EXAMPLE 15

200 mg of vitamin $K_1$ are dissolved in 1 ml of glycerol 1,2-dimethyl ether, there being obtained a clear solution.

EXAMPLE 16

200 mg of tocopherol are dissolved in 1 ml of glycerol 1,2-dimethyl ether, there being obtained a clear solution.

What is claimed is:

1. A pharmaceutical preparation comprising an effective amount of a vitamin selected from the group consisting of vitamin A acetate, vitamin $K_1$ and vitamin E and a solvent containing a glycerol lower-alkyl ether selected from glycerol 1-methyl ether, glycerol 1-ethyl ether, glycerol 1,3-dimethyl ether and glycerol, 1,2-dimethyl ether, said glycerol lower-alkyl ether and said solvent being present in an amount sufficient to dissolve said active ingredient.

2. The preparation of claim 1 wherein said ether is present in said solvent in an amount of at least 50% by volume.

3. The preparation of claim 2 wherein the glycerol lower-alkyl ether is a glycerol mono(lower-alkyl)ether or a glycerol di(lower-alkyl)ether.

4. The preparation of claim 3 wherein the glycerol lower-alkyl ether is glycol 1,2-dimethyl ether, glycerol 1-methyl ether or glycerol 1,3-dimethyl ether.

5. The preparation of claim 2 wherein the solvent contains 50% to 80% by volume of a glycerol lower-alkyl ether and 20% to 50% by volume of water.

6. The preparation of claim 5 wherein said solvent contains ethanol.

* * * * *